United States Patent [19]

Finney et al.

[11] Patent Number: 4,550,719
[45] Date of Patent: Nov. 5, 1985

[54] IMPLANTABLE PENILE ERECTILE SYSTEM

[75] Inventors: Roy. P. Finney, Tampa, Fla.; Robert E. Trick; Henry W. Lynch, both of Racine, Wis.

[73] Assignee: Medical Engineering Corporation, Racine, Wis.

[21] Appl. No.: 571,902

[22] PCT Filed: Feb. 14, 1983

[86] PCT No.: PCT(US83/00196
§ 371 Date: Nov. 9, 1983
§ 102(e) Date: Nov. 9, 1983

[87] PCT Pub. No.: WO84/03038
PCT Pub. Date: Aug. 16, 1984

Related U.S. Application Data

[63] Continuation-in-part of Ser. No. 289,879, Aug. 4, 1981, Pat. No. 4,399,811.

[51] Int. Cl.[4] ............................................. A61F 5/00
[52] U.S. Cl. .......................................... 128/79; 623/14
[58] Field of Search ................................. 128/79; 3/1

[56] References Cited

U.S. PATENT DOCUMENTS

| | | | |
|---|---|---|---|
| 3,853,122 | 12/1974 | Strauch et al. | 128/79 |
| 4,201,202 | 5/1980 | Finney et al. | 3/1 |
| 4,267,829 | 5/1981 | Burton | 128/79 |
| 4,318,396 | 3/1982 | Finney | 128/79 |
| 4,353,360 | 10/1982 | Finney et al. | 128/79 |
| 4,360,010 | 11/1982 | Finney | 128/79 |
| 4,364,379 | 12/1982 | Finney | 128/79 |
| 4,369,771 | 1/1983 | Trick | 128/79 |
| 4,383,525 | 5/1983 | Scott et al. | 128/79 |
| 4,399,811 | 8/1983 | Finney et al. | 128/79 |
| 4,407,278 | 10/1983 | Burton et al. | 128/79 |

Primary Examiner—Paul J. Hirsch
Attorney, Agent, or Firm—Quarles & Brady

[57] ABSTRACT

A penile erectile system which is adapted to be surgically implanted in man for the treatment of erectile impotence includes at least one penile implant comprising an elongated, flexible cylindrical body (11, 11') adapted to be implanted in the corpus cavernosum of a penis, said body having a tip (14) at one end and an anchoring stem (12) at the other end and an intermediate section (13) including a pair of inner (17) and outer (18) chambers substantially filled with fluid (20) and connected by a passage (21). The body (11, 11') also includes internal pump means (19) adjacent the stem for transferring fluid into the inner chamber (17) and a control valve (29) adjacent the tip (14) for controlling pressure in the inner chamber (17). The inner chamber (17) is non-distensible so that when it is filled and pressurized by transferring fluid thereto it becomes rigid and supports the penis in an erectile state.

3 Claims, 9 Drawing Figures

IMPLANTABLE PENILE ERECTILE SYSTEM

This is a continuation in part of Ser. No. 289,879, filed Aug. 4, 1981, now U.S. Pat. No. 4,399,811.

TECHNICAL FIELD

The present invention relates to a novel implantable penile erectile system. More particularly, it relates to an implantable penile erectile system which can be pressurized to effect an erection and thus is useful in the treatment of erectile impotence.

BACKGROUND ART

Some cases of erectile impotence do not respond to conventional therapy and, as a result, the surgical implanting of a penile erectile system may be the only practical means of remedying the impotency.

In the past, several different types of penile erectile systems have been employed. One type of penile erectile system which is currently available is an inflatable system which includes two inflatable and distensible tubes both of which are surgically implanted in the corpora cavernosa of the penis. Each of the two tubes is connected by tubing to a relatively large reservoir of inflating fluid which is implanted elsewhere in the body necessitating additional abdominal surgery.

Another type of penile erectile system in use comprises a pair of rods of suitable stiffness which are surgically implanted into the corpora cavernosa of the penis. A significant advantage of this system is that the amount of surgery involved is minimal as there is no pressure bulb to implant. A disadvantage of this system is that the permanent stiffness of the rods can be a source of physical pain and embarrassment to the patient.

DISCLOSURE OF THE INVENTION

It is the general object of the present invention to disclose a novel implantable penile erectile system which when non-pressurized allows the penis to assume a normal flaccid state and which can be pressurized to effect an erection.

It is a further object to disclose such a pressurizable implantable penile erectile system that can be implanted completely in the penis making abdominal or scrotal surgery unnecessary.

In the preferred embodiment the penile erectile system consists of two identical, independent self-contained, pressurizable implants which can be surgically implanted completely within the penis as easily as implanting a prior art rod type implant.

The implants of the preferred embodiment of the penile erectile system of the present invention each have a relatively short, proximal stem, a distal tip and an elongated flexible intermediate poriton containing a pair of concentric cylindrical chambers. In the non-pressurized state both of the chambers of the implant which are substantially filled with hydraulic fluid are connected by a passage so that the hydraulic fluid present in the outer chamber can be transferred to the inner chamber which is non-distensible to pressurize it and make it rigid. The preferred implant also includes pump means adjacent the stem for transferring fluid under pressure from the outer chamber to the non-distensible inner chamber and a pressure control valve adjacent the tip which can be used to limit the pressure in the inner chamber and to depressurize it. The implants, which comprise tne entire penile erectile system, can be implanted in the corpora cavernosa in the same manner as the prior art penile rod implants.

When the preferred implants are in place, the inner chambers of the implants are pressurized by pumping the hydraulic fluid from the outer chambers into the non-distensible inner chambers under pressure making them to become rigid and causing the penis to assume an erectile position.

The penile erectile system of the present invention, in addition to being compact and thus minimizing the amount of surgery required, also has the advantage of having a minimum number of fluid connections, thus reducing the risk of leakage.

BEST MODE OF CARRYING OUT THE INVENTION

The preferred embodiment of the penile erectile system of the present invention, which is shown in FIGS. 1-4, comprises a pair of elongated penile implants 11, 11'. The two implants 11, 11' are identical, therefore, only one will be described in detail.

Figure 1:
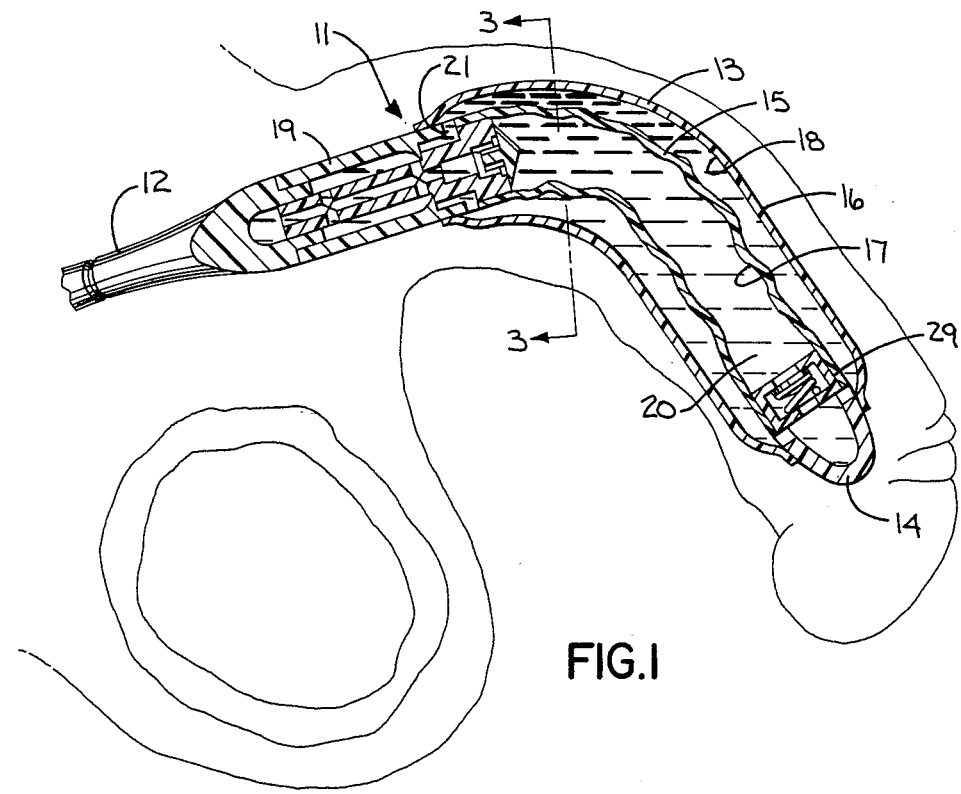
FIG. 1 is a side view, partly in section, of the preferred embodiment of the penile erectile system of the present invention showing one of the two identical penile implants surgically implanted in a male and in a non-pressurized condition.
Figure 2:
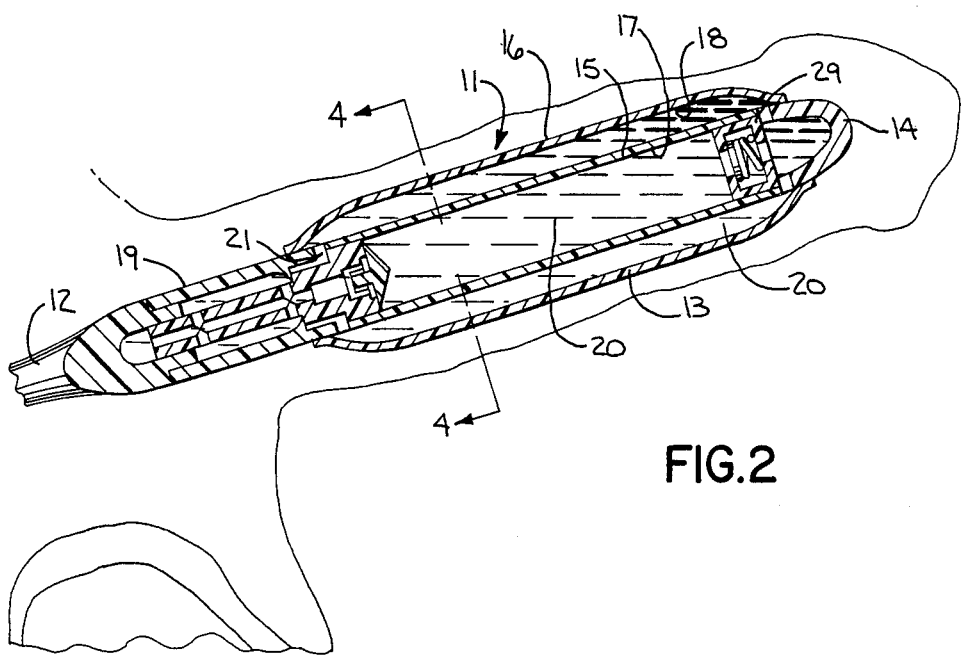
FIG. 2 is a side view similar to FIG. 1, except that the implant is pressurized.
Figure 3:
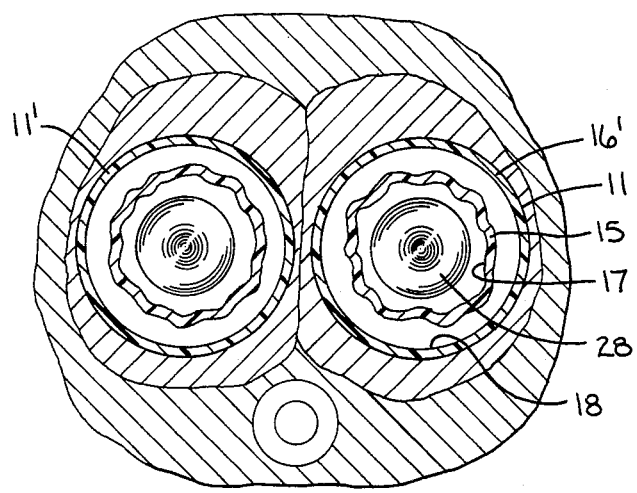
FIG. 3 is an enlarged cross sectional view taken along the line 3—3 in FIG. 1.
Figure 4:
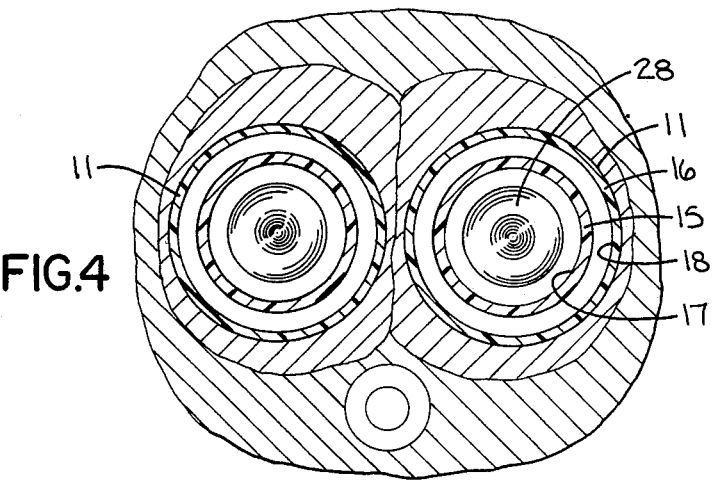
FIG. 4 is an enlarged cross sectional view taken along the line 4—4 in FIG. 2.

As seen best in FIGS. 1 and 2, the implant 11 has a short, proximal stem 12, an intermediate cylindrical portion 13, and a conical distal tip 14. The stem 12 which is of a relatively stiff material is implanted in the root end of a corpus cavernosum and the cylindrical portion 13 and the tip 14 which are soft and relatively flexible are implanted in the portion of the corpus cavernosum in the pendulus penis. As seen in FIGS. 3 and 4, each of the implants 11, 11' is positioned in a separate corpus cavernosum of the penis.

The intermediate cylindrical portion 13 of the implant 11 includes a pair of concentric cylindrical sleeves 15 and 16 which are attached in a fluid tight manner to the stem 12 and to the tip 14 to form a pair of concentric chambers 17 and 18, respectively. The sleeve 15 which forms the wall of the inner chamber 17 is of an inelastic material such as a silicone coated mesh or woven fabric so that the chamber 17 is non-distensible even when pressurized. The sleeve 15 also cooperates with the sleeve 16 which is spaced outwardly from the sleeve 15 to form the outer chamber 18. The sleeve 16 may be made of a distensible material such as non-reinforced silicone rubber. The necessary fluid tight seals between the sleeves 15 and 16 and the stem 12 and tip 14 may be made with a suitable adhesive or by other suitable means.

As seen in FIGS. 1 and 3, when the implant 11 is in a non-pressurized state both the chambers 17 and 18 are substantially filled with a non-compressible hydraulic fluid 20 which may be a biocompatible fluid such as saline or a free flowing silicone gel. In the non-pressurized state, the soft, flexible, intermediate cylindrical portion 13 of the implant 11 flexes and permits the penis to assume a substantially normal, flaccid position as seen in FIG. 1. However, when the implant 11 is in the pressurized state as seen in FIGS. 2 and 4 the intermediate cylindrical portion 13 is rigid as the result of the non-distensible inner chamber 17 being completely filled with fluid under pressure and the penis assumes an erectile position.

The pump means, generally referred to as 19, for pressurizing the inner chamber 17 and the pressure control valve 29 for limiting the fluid pressure in the chamber 17 will now be described.

Figure 5:
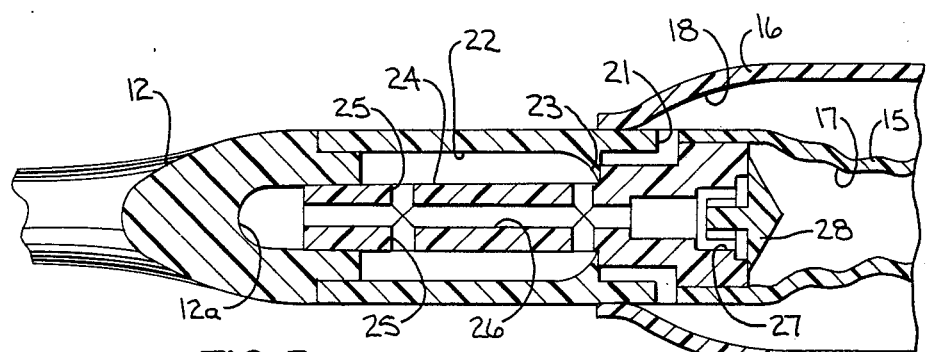
FIG. 5 is an enlarged view, partly in section, of the proximal stem portion of the implant of FIG. 1 showing the position of the pump components when the inner chamber is not pressurized.
Figure 6:
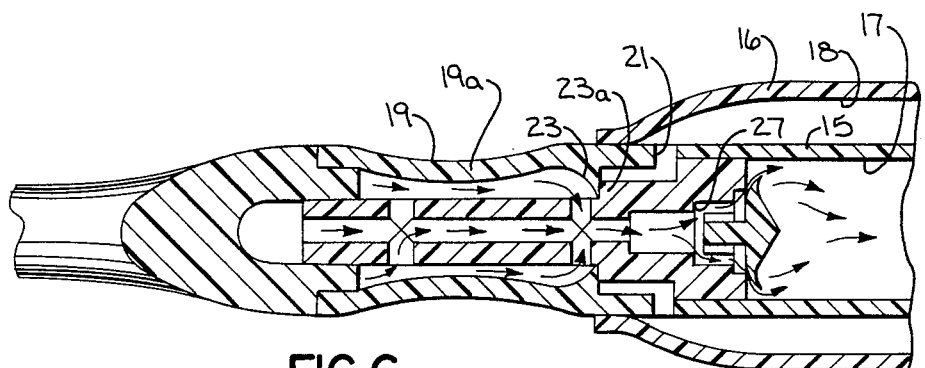
FIG. 6 is an enlarged view similar to that of FIG. 5 showing the position of the pump components when the pump is being used to pressurize the inner chamber.
Figure 7:
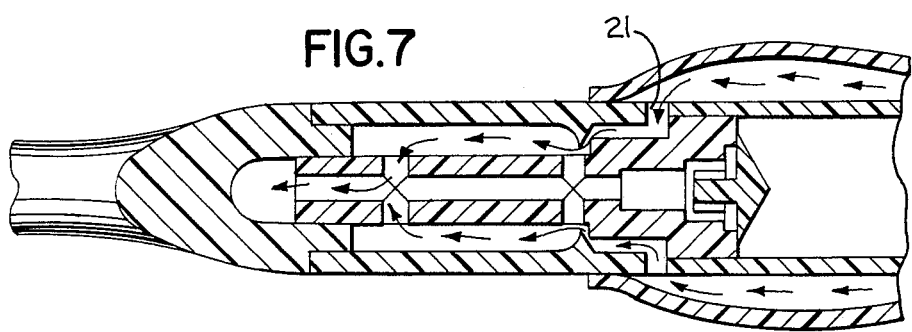
FIG. 7 is an enlarged view similar to that of FIG. 5 showing the pump components when the fluid is flowing from the outer chamber to the pump chamber.

As seen in FIGS. 5, 6 and 7, there is a passage 21 in the proximal portion 12 of the implant 11 which leads from the outer chamber 18 to the pumping chamber 22 of the pump 19. As seen in FIG. 7, the exit of the passage 21 is normally closed by a one way flap valve 23 which opens when the fluid pressure on the valve 23 in the passage 21 exceeds that in the pumping chamber 22 as seen in FIG. 7.

Positioned within the pumping chamber 22 is a support member 24 which has axial passages 25, 25' and a longitudinal passage 26 extending therethrough. The support member 24 extends from and provides communication between the hollow interior 12a of the proximal stem 12, the pumping chamber 22 and the inner chamber 17. The end of the passage 26 opposite the proximal stem 12 has an enlarged exit 27 in which there is positioned an umbrella type flexible check valve 28. The check valve 28 is normally kept seated closing the passage 26 by the fluid pressure in chamber 17. However, when the wall of the pump 19 is squeezed as shown in FIG. 6 the fluid pressure in the pumping chamber 22 and passage 26 exceeds that in chamber 17 and the check valve 28 is opened allowing fluid to flow about the check valve 28 into chamber 17 as indicated by the arrows.

The implant 11 is pressurized by sequentially squeezing the resilient wall 19a of the pump 19 to force the hydraulic fluid 20 under pressure from the pumping chamber 22 into non-distensible inner chamber 17 under pressure and allowing the wall 19a to assume its normal shape. When the pump wall 19a is first squeezed the fluid 20 originally in the pumping chamber 22 is forced through the axial passages 25 and longitudinal passage 26 out the exit 27 forcing the check valve 28 off its seat allowing the fluid 20 to flow about the valve 28 into the chamber 17 (as shown by the arrows in FIG. 6). The increased pressure in the pumping chamber 22 keeps the flap valve 23 seated closing passage 21. Thereafter, when the wall 19a is allowed to assume its normal position, a reduced pressure is formed in the pumping chamber 22 as a result the flap valve 23 is moved off its seat 23a allowing fluid 20 to flow from chamber 18 to enter the pumping chamber 22. When the pressure in pumping chamber 22 equals or exceeds that in chamber 18 the flap valve 23 closes the passage 21. When the chamber 17 is sufficiently pressurized and rigid, the pumping is stopped whereby the exit 27 of the passage 26 is closed by the fluid pressure of the hydraulic fluid 20 in chamber 17 upon the outer surface 28a on the enlarged head of the check valve 28. As a result, the chamber 17 remains filled, pressurized and rigid, as seen in FIG. 2, until the control valve 29 (seen in FIGS. 8 and 9) is opened allowing the fluid 20 to flow via passage 30 back to the chamber 18 whereupon the implant 11 resumes a non-pressurized state.

The filling and pressurizing of the non-distensible inner chamber 17 may be facilitated by manually squeezing the penis in the area about the outer chamber 18 to help force the fluid 20 which is in that chamber through the passage 21, past the flap valve 23 and into the pumping chamber 22.

Figure 8:
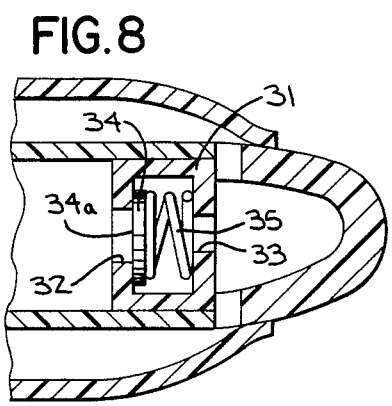
FIG. 8 is an enlarged view, partially in section, of the distal tip portion of the implant of FIG. 1 showing the position of the valve components when the value is closed.
Figure 9:
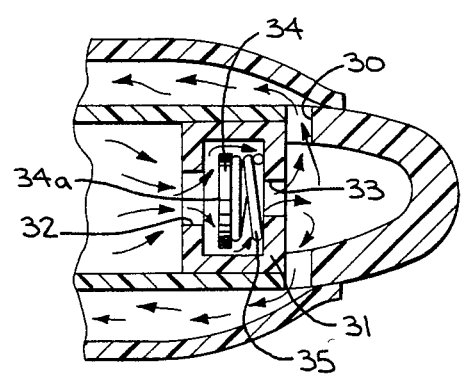
FIG. 9 is an enlarged view similar to that of FIG. 8 showing the position of the valve components when the valve is open.

The preferred pressure control valve 29 which is shown in FIGS. 8 and 9 can be manually opened by squeezing or it will automatically open when the pressure in the chamber 17 exceeds a predetermined level. The valve 29 consists of a valve housing 31 having an inlet 32 and an outlet 33. Located within the housing 31 between the inlet 32 and the outlet 33 is a sealing member 34 and a precalibrated spring 35 which is positioned between the sealing member 34 and the outlet 33. The precalibrated spring 35 normally holds the sealing member 34 seated about the inlet 32 which leads from the inner chamber 17 into the housing 31. When the pressure in the inner chamber 17 which is sensed by the central portion 34a of the sealing member, exceeds the holding force of the precalibrated spring 35 the sealing member 34 is automatically moved from its normal seated position closing the inlet 32 and fluid flows from the inner chamber 17 into the housing 31 and out the outlet 33 and via the passage 30 into the outer chamber 18. Once the pressure sensed by the portion 34a of the sealing member drops below the predetermined level, the calibrated spring 35 reseats the member 34 in its normal position closing the inlet 32.

When it is desired to depressurize the chamber 18 of the implant the valve 29 may be manually opened by squeezing the housing 31 to deform it, thus moving the member 34 away from its normal position closing the inlet 32. Alternatively, the chamber 18 may be depressurized by squeezing the penis and the implant with sufficient force to cause the pressure in chamber 17 to exceed the safe level thereby opening the valve 29 and then continuing the squeezing force until the chamber 17 is sufficiently empty so that the penis will assume a flaccid state. Other types of pressure control valves, of course, may also be used.

The non-distensible inner chamber 17 of the penile implants must when pressurized provide rigidity sufficient to maintain the penis in an erectile position. Therefore, it must be of sufficient volume and size to perform this function either alone or in combination with another implant. In contrast, the outer chamber 18 serves primarily as reservoirs of pressurizing fluid for inner chambers and are sized accordingly. The exact dimensions of the inner and outer chambers are not critical as long as they are adequate to provide their desired function.

The sleeve 15 which forms the wall of the "non-distensible" chamber 17 must be relatively inelastic and is preferably made of a dacron mesh or fabric covered with silicone material that will not stretch when filled with fluid and pressurized. In contrast, the sleeve 16 may be either distensible or non-distensible. The diameters of the sleeves 15 and 16 can vary but are normally sized so that the implant in the non-pressurized state will fill the corpora cavernosa. It will be appreciated that the term non-distensible or inelastic is intended to cover any material which possesses the desired properties which enable it to provide its described function.

The proximal stem 12 of the implant preferably has a Shore A hardness of about 70, the distal tip 14 a Shore A hardness of about 20, and each of the materials has sufficient tensile strength for its intended use. In the preferred embodiments of the drawings, the tip is tapered and is made of a self-sealing silicone elastomer which allows fluid to be added to or removed from the implant with a fine hollow needle and a syringe.

The term "substantially filled" as used herein to describe the fluid content of a chamber means that a chamber contains about 60% to about 95% or more of its capacity of a non-compressible fluid such as water, saline or a free flowing gel. The actual content of fluid can vary; however, the implant when "substantially filled" should be still sufficiently flexible so that the penis can assume a normal flaccid position.

All the parts and components of the prosthesis are preferably made of or covered with medical grade silicone rubber which is non-reactive, non-toxic and well tolerated by the adjacent organic tissues. Silicone rubber is preferred because it is quite resistant to wear and remains functional for long periods of time. However, other suitable materials possessing desirable properties may also be employed.

The preferred method of implantation of the erectile system is through an incision made in the penis. After appropriate incision, each corpus cavernosum is dilated distally and proximally to accept the implants. The appropriate anatomical measurements are made to insure that the proximal end of the implant or implants will be positioned at the base of the penis below the pelvic bone. Preferably, the pump is located at the penile base partly under the pubic bone. An implant or implants having an appropriately sized intermediate section and distal tip is inserted into the corpus cavernosum of the penis. The distal tip is positioned in the glans end of the corpus cavernosum. The stem at the proximal end of the implant then is anchored in the root end of the corpus cavernosum.

The identical procedure is performed on the other side of the penis to complete the surgical procedure. The stems of the two implants preferably will diverge laterally to accommodate the anatomy, to provide lateral stability of the penis and to prevent rotation of the implants. The incision is then closed.

It is to be understood that the foregoing description has been for purposes of illustration and that a number of modifications and changes may be made without departing from the spirit and scope of the present invention. For example, although the implants described have solid stems for anchoring the implants, the stems could be hollow, if desired. In addition, although implants have been described and illustrated in which the outer chamber which serves as the reservoir is concentric relative to the inner chamber it will be appreciated that the reservoir role could be provided by one or more radially disposed smaller individual outer chambers if desired. It also will be appreciated that, if desired, the inner chamber 17 may contain a central rod to reduce its volume or provide support. In addition, it will be understood that in some instances a single implant may be used in place of the two implants of the preferred embodiment.

The embodiments of the invention in which an exclusive property or privilege is claimed are defined as follows:

1. In a penile erectile system including a penile implant having an elongated unitary body with a tip at one end and an anchoring stem at the other end and including an intermediate inner chamber with a radially disposed outer chamber, the inner chamber being non-distensible so that when pressurized and filled with fluid it becomes rigid; a passage providing communication between said inner and outer chambers; pump means within the body for transferring fluid from the outer chamber into the inner chamber to pressurize it and make it rigid and a control valve for controlling the pressure in said inner chamber, the improvement which comprises an improved control valve located adjacent the tip, said valve including a housing having an inlet communicating with the inner chamber and an outlet communicating with the outer chamber, a sealing member for the inlet in the housing and a precalibrated spring positioned in the housing, between the sealing member and the outlet, said spring normally holding the sealing member against the inlet, said valve automatically opening when the pressure in the inner chamber exceeds the force of the precalibrated spring.

2. The implant of claim 1 in which both chambers are normally substantially filled with hydraulic fluid and the outer chamber contains enough fluid which can be transferred to fill and pressurize the inner non-distensible chamber.

3. The implant of claim 1 which includes a tapered, hollow tip of self-sealing material.

* * * * *